United States Patent [19]

Sasaki et al.

[11] 4,131,668

[45] Dec. 26, 1978

[54] IRON ORE PELLET PROCESS CONTROL

[75] Inventors: Minoru Sasaki; Kaoru Ito, both of Yokohama; Katsuhiro Minamida, Kawasaki; Keiki Fujita, Himeji, all of Japan

[73] Assignee: Nippon Steel Corporation, Tokyo, Japan

[21] Appl. No.: 707,570

[22] Filed: Jul. 21, 1976

Related U.S. Application Data

[63] Continuation-in-part of Ser. No. 516,663, Oct. 2, 1974, abandoned.

[30] Foreign Application Priority Data

Mar. 15, 1974 [JP] Japan ................................. 49-29721

[51] Int. Cl.² ............................................. B01J 2/12
[52] U.S. Cl. ............................... 264/40.4; 264/40.6; 264/117
[58] Field of Search ................... 264/117, 40.4, 40.6

[56] References Cited

U.S. PATENT DOCUMENTS

| 3,328,843 | 7/1967 | Murphy, Jr. et al. | 264/40.4 |
| 3,450,529 | 6/1969 | MacDonald | 264/40.4 |

Primary Examiner—Robert F. White
Assistant Examiner—James R. Hall
Attorney, Agent, or Firm—Toren, McGeady and Stanger

[57] ABSTRACT

A method for controlling an iron ore pelletizing and pellet processing operation by evaluating the results of the on-stream analysis of the apparent specific gravity or apparent density distributions of the dry and fired pellet samples which permits the operator of the process to determine if any changes in the process control factors are required in order to impart into the fired pellets an apparent specific gravity or apparent density distribution optimized therefor as the fired pellets are used as a blast furnace charge composition. The method includes the use of an apparent specific gravity measuring step wherein a pellet process stream is periodically sampled and the pellet samples are presented in sequence to a weight measurement unit capable of producing an electric signal proportional to the weight of each sample, from which it proceeds into a volume measurement unit photoelectrically responsive thereto to produce an electric signal proportional to the volume of the sample. A computer is provided in response to the electric signals to compute the apparent specific gravity of each of the samples. This permits a rapid and accurate record of sample analysis to be maintained for the effective control of the process factors.

5 Claims, 11 Drawing Figures

IRON ORE PELLET PROCESS CONTROL

CROSS REFERENCE TO RELATED APPLICATIONS

This application is a continuation-in-part of U.S. Patent Application Ser. No. 516,663 filed Oct. 2, 1974, now abandoned, based on a Japanese priority application No. Sho 49-29721 filed Mar. 15, 1974.

FIELD OF THE INVENTION

This invention relates to the production of iron ore pellets which are particularly adapted for use in a blast furnace, and, more particularly, to a method for controlling pelletizing and pellet processing operation in dynamic response to evaluation of the results of apparent specific gravity distribution analysis of dry and fired pellets sampled from a process stream to stabilize the quality of the final product at a high level.

BACKGROUND OF THE INVENTION

As the proportion of blast furnace charge compositions in pelletized form of iron ores increases due to the excellent adaption of pellet properties thereto, increasing requirements are directed not only to the feature that the processed pellets, being regarded merely as a mass of particles, possess an excellent overall quality with respect to crushing strength, reducibility and reduction swelling, but also the feature that the individual pellets have qualities with as small an unevenness as possible. It is known that the quality of a pellet depends upon many factors, for example, the pelletizer charge composition (blend ratio of different source iron ores, mineralogical composition, chemical composition and size distribution), pretreating parameters (moisture content and mixing time), pelletizing parameters (rate of rotation of the pelletizer, inclination angle, volumetric depth and average retention time), drying parameters (temperature and rate), firing parameters (heat pattern and atmosphere) and cooling parameters (temperature and rate); these factors influencing one another in a complex manner.

Prior art pelletizing systems have generally ignored variations in charge composition which may occur in a short period of time, for example, in a single production run, and have permitted for the process operator to determine the control factors in the subsequent steps in the process, assuming that the initial charge composition does not vary. Even if samples or assay were periodically cut from the process stream on a short time interval cycle in sequence, the assay information would not be available until from several hours in the swift case and usually not until the next day. By this time, the parameters of the process had, in all likelihood, altered so significantly that any changes made in the processing based on the sample assay results would be useless.

On the other hand, more recently, there has been an increasing tendency to use finely-divided iron ores which are transported in slurry form and stored in the settling pond, and dry powder of iron ore after the screening thereof has been seen in making blast furnace charge composition. Further, it has become a frequent practice to blend a plurality of iron ores of different sources and additional ingredients such as lime and dolomite in various ratios. As a result, it is practically impossible to avoid some variations with time of size distribution and compositional ranges of the constituents in the composition which is to be supplied to a pelletizer.

FIG. 1 shows an example of such variations in percentage of particular size particles and a constituent, in this instance, $SiO_2$, in the starting material used in a pellet manufacturing plant. This problem can not be solved unless further information than the results of the chemical analysis and size distribution assay made at such a low frequency as one time a day or a production run are provided. Even if the sampling frequency is increased, the prior art system cannot control the pelletizing and pellet processing operation in any optical fashion because of the high rate of processing and the multiplicity of control factors as has been described above.

An investigation of the present inventors has indicated that fired pellets as the final product, though sampled from the same production run, have qualities different from one another, which qualities are distributed over a considerably wide range. These qualities are related to the apparent specific gravities (or apparent densities) of the respective pellets as shown in FIG. 2. Further investigations have led us to a finding that the reason why the qualities of the fired pellets are distributed over such a wide range is based on the fact that insufficient pretreatment of the pelletizer change composition and inappropriate control of the pelletizing parameters impart different apparent specific gravities to different green pellets which are to be presented to a firing furnace, and that such a distribution range is further extended by heat pattern variation which may occur in the firing furnace.

BRIEF DESCRIPTION OF THE DRAWINGS

The present invention may be better understood by reference to the accompanying drawings in which.

DETAILED DESCRIPTION OF THE INVENTION

The invention will next be described in connection with the results of the following experiment using an iron ore of analysis A in Table 1 given below.

Table 1

| Constituent | Analysis (percent by wt.) | |
|---|---|---|
| | A | B |
| Total Fe | 69.62 | 65.60 |
| $SiO_2$ | 0.34 | 4.01 |
| $Al_2O_3$ | 0.21 | 1.61 |
| CaO | 0.53 | 4.68 |
| MgO | 0.88 | 0.29 |
| Size distribution | | |
| −325 mesh (%) | 79.9 | 75.0 |
| Blain Index | 1800 | 3250 |

Figure 1:
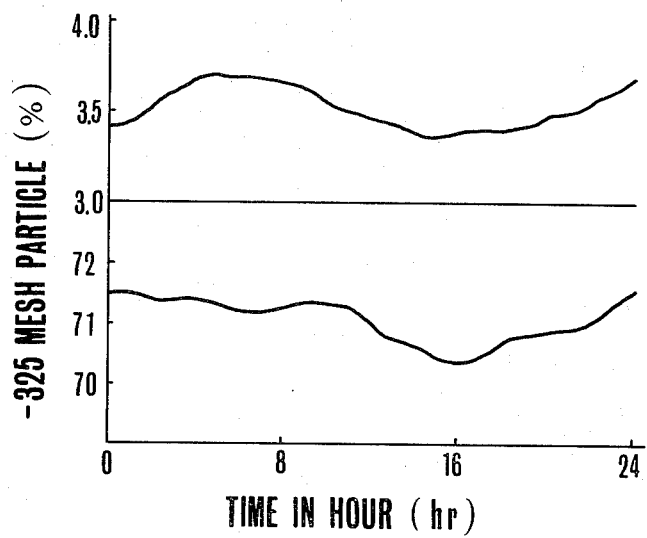
FIG. 1 is a graph depicting variations with time of the percentages of particular size particles and a constituent in a pelletizer charge composition.
Figure 2:
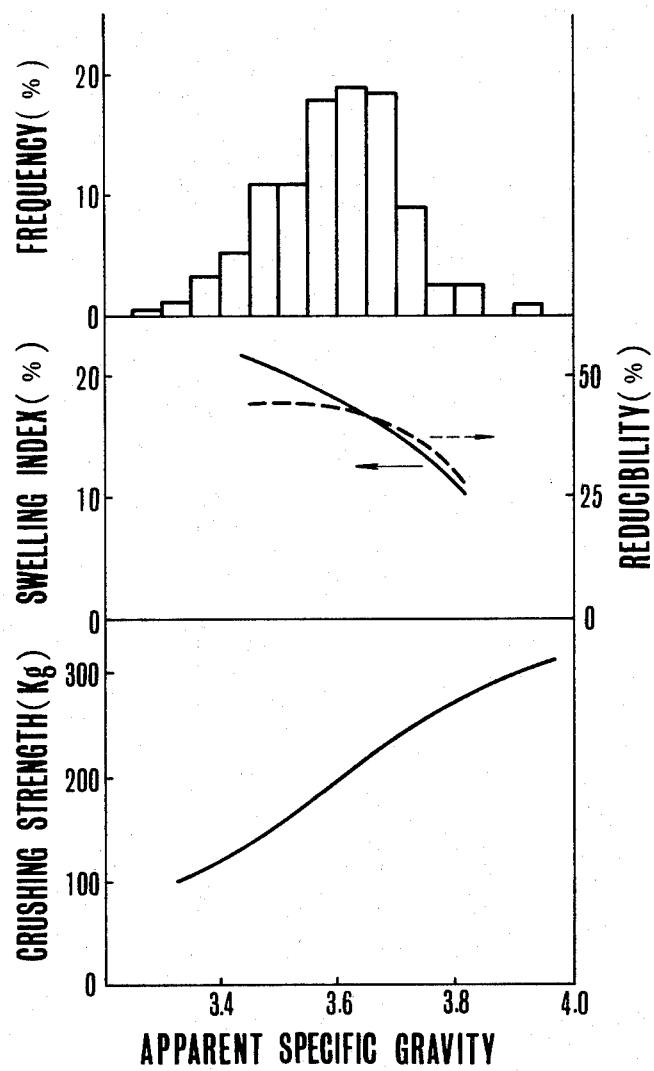
FIG. 2 is a graph relating the apparent specific gravities of fired pellets to their respective properties.
Figure 3:
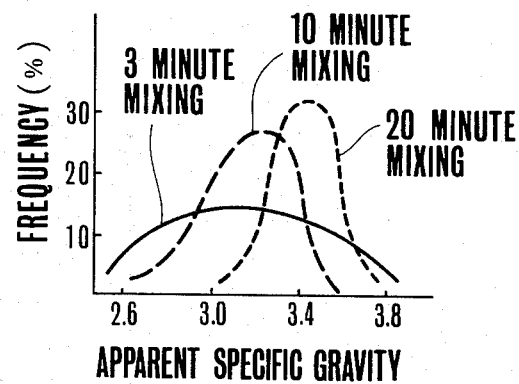
FIG. 3 is a graph depicting the variation of apparent specific gravity distribution of green pellets with respect to the mixing time for the mixture containing powdered iron ore and water.

Three mixtures each containing finely-divided iron ore A and 6% by weight of water were prepared with respective compounding times, each of which was fed from a mixer of 50kg vessel capacity to a pelletizer of 100 cm$\phi$ operating at a rate of rotation of 7 rpm on an average retention time of 6 minutes. As is evident from FIG. 3, the insufficient compounding of the mixture results in an extended distribution range of the apparent specific gravities of the resulting green pellets. The variation in the water content also affected the extension of the distribution range to a large extent.

Figure 4:
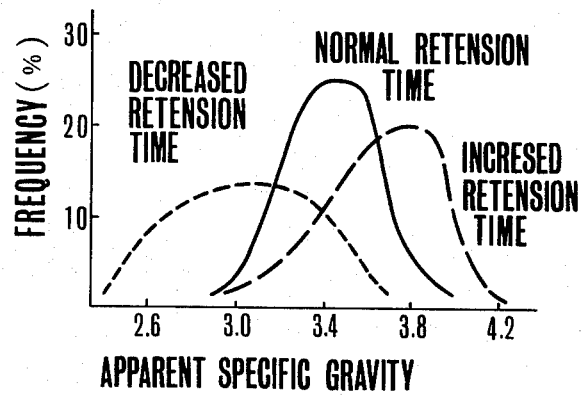
FIG. 4 is a graph depicting the variation of apparent specific gravity distribution of green pellets with respect to the retention time in a pelletizer.

With a sufficiently compounded mixture, it was observed that the distribution range of the apparent specific gravities of green pellets was extended considerably either when the retention time in the pelletizer was increased too much, or when it was decreased too much. The results are shown in FIG. 4. Other pelletizing operation control parameters such as the rate of rotation of the pelletizer, the angle of inclination of the pan and the volumetric depth of the mixture in the pelletizer also affected the variation of the distribution range in secondary manner. When the green pellets were dried to dewater, the apparent specific gravity distribution of the dry pellets was almost identical in shape to that of the green pellets and was hardly affected by variation of the drying conditions.

Figure 5:
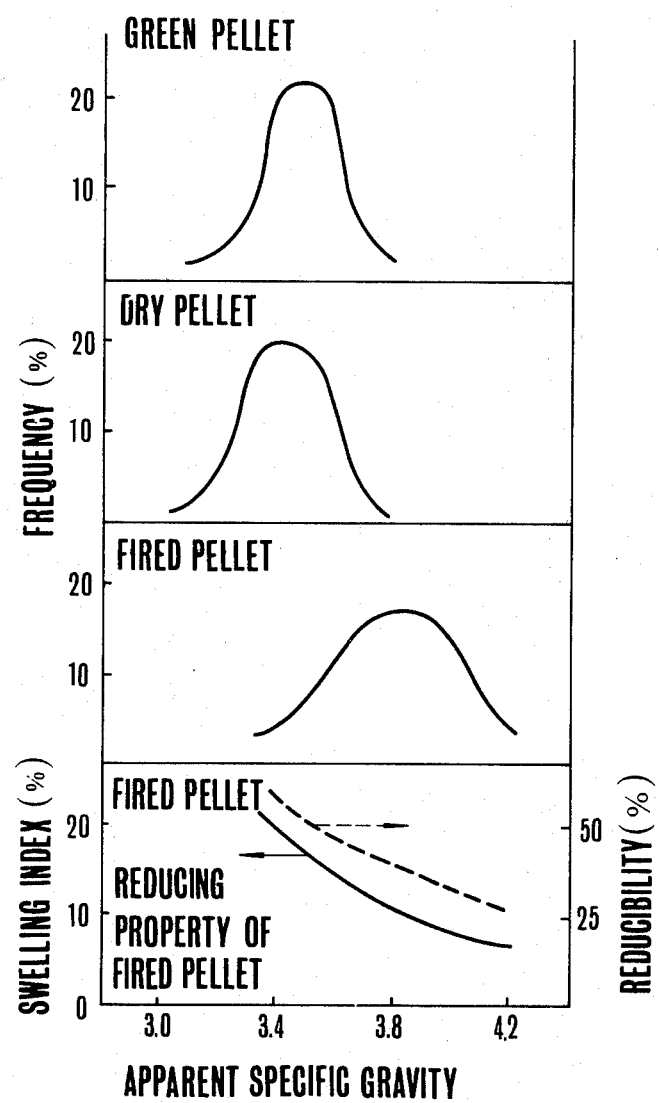
FIG. 5 is a graph depicting how the apparent specific gravity distribution of green pellets is varied after the drying and firing of the green pellets and to what extent the apparent specific gravities of the fired pellets are related to their respective reduction properties; ;p

When the dry pellets were fired in a certain heat pattern, the distribution range of the apparent specific gravities of the resulting pellets was made wider than that of the apparent specific gravities of the dry pellets. The shifting and widening of the distribution range are depicted in FIG. 5. Of course, it is possible to control the shifting and widening quantities by varying the heat pattern adapted to the dry pellets in the same lot. Conversely, it is to be understood that this phenomenon can be utilized to maintain a constant distribution of the apparent specific gravities of the fired pellets during the entire production run despite variation of the apparent specific gravity distribution of the dry pellets.

We have thus discovered a system for controlling an iron ore pelletizing and pellet processing operation which permits the process operator to evaluate the apparent specific gravity distributions of the dry and fired pellets as determined from the on-stream sample assay. Certain pretreating and pelletizing parameters can then be immediately altered so as to be optimum for ever-varying compositions of the supplied starting material and certain firing parameters so as to be optimum for the resultant dry pellets, so that the final pellets thus produced come up to a desired even quality.

In order to increase the effectiveness of this system in practice, we have devised a rapid apparent specific gravity measuring instrument which is particularly adapted for use in the system. According to JIS, the mercury method has to be employed in measuring the apparent specific gravity of a pellet and has been applied to general specific gravity measurements. However, this method takes a considerably long time for the measurement, for example, several tens of hours for an expert to measure the apparent specific gravities of from 400 to 500 pellets which are necessary to determine a reliable distribution curve. Moreover, the mercury vapor is very poisonous to the human body.

The operating principle of the rapid specific gravity (or density) distribution finding instrumentation used in the method of the invention is as follows. Pellet samples are presented in sequence to a weight measurement section capable of generating an electric signal proportional to the weight of a pellet from which it proceeds into a volume measurement section in which the pellet is transported by a suitable means past a beam of parallel light rays projected from an elongated slit onto a photoelectric element. The photoelectric element is capable, upon detection of those portions of the beam which are blocked by the moving pellet, of producing outputs which are integrated with respect to time to provide an electric signal proportional to the volume of the pellet. The first- and second-named electric signals are sequentially transmitted to a computer to calculate a number of apparent specific gravities which are necessary for accurately controlling certain processing parameters.

Figure 6:
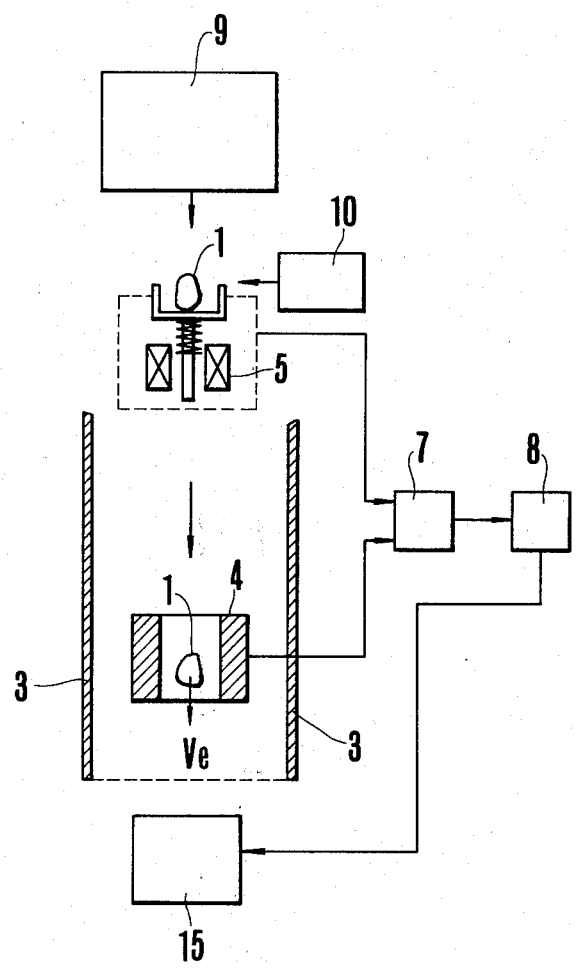
FIG. 6 is a schematic sectional view, partially in block form, of an instrument for rapid and accurate measurement of the apparent specific gravity of a pellet which instrument may be used in accordance with the method of the present invention.

Referring now to FIG. 6, an instrument for measuring the apparent specific gravities of pellets in sequence embodying one form of the invention is schematically illustrated as including a sampling mechanism 9 for selecting a pellet 1 in sequence from a process stream. The pellet 1 selected by the sampler 9 is diverted into a weight measurement unit 5, after the weight of the pellet 1 having been measured thereby, from which the pellet is caused by a pellet-advancing mechanism 10 to proceed into a windshield tube 3, dropping through a volume measurement unit 4 to a specific gravity classifier 15. Electrical signals from the volume and weight measurement units 4 and 5 are sequentially transmitted to a computer which in response thereto derives an output representative of the specific gravity of the pellet. Responsive to the output which is displayed by a recorder or printer 8, the classifier 15 classifies the incoming pellets with respect to the computed specific gravity.

Figure 7:
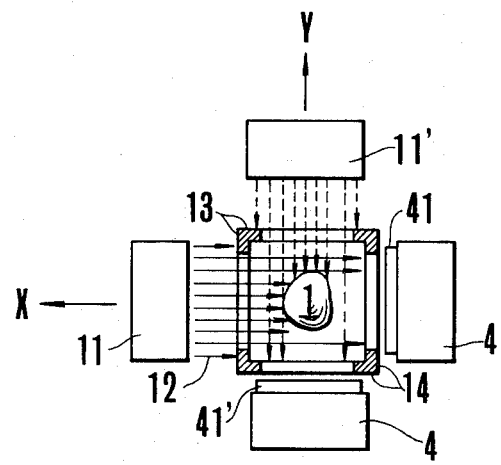
FIG. 7 is a schematic partially elevational partially sectional view of a volume measuring section taken in X-Y plane of the instrument of FIG. 6.
Figure 8:
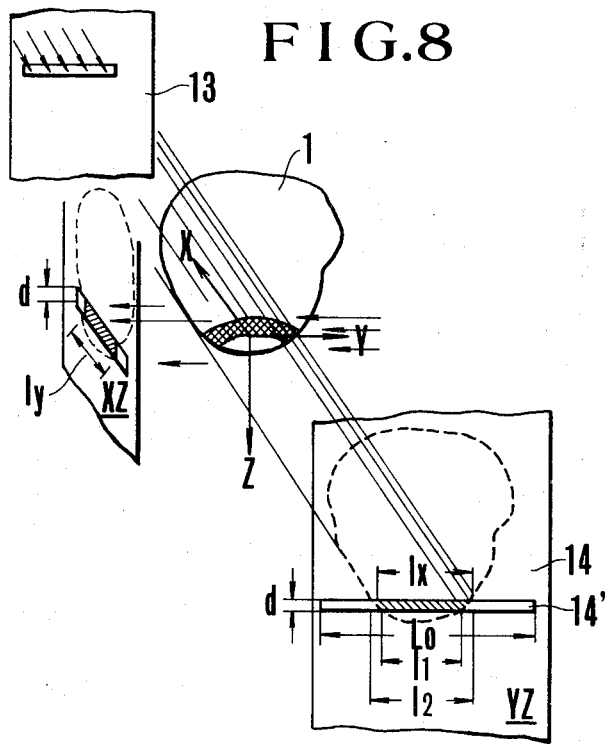
FIG. 8 is a fragmentary enlarged perspective view illustrating the principle of measuring the volume of a pellet.

A more detailed construction of the volume measurement unit 4 and its function of measuring a pellet volume will be better understood by reference to FIGS. 7 and 8. A pellet 1 drops past a beam 12 of parallel light rays projected through a horizontally elongated slit 13 from a light source 11 onto a photoelectric element 41, the element 41 being provided with a slit 14' having a length, $L_o$, and a width, d, positioned in front thereof, so that when portions of the beam are blocked by the dropping pellet, the photoelectric element 41 produces outputs proportional to the respective blocked beam portions.

As is evident from FIG. 8, when the shadow of a pellet on a YZ plane has an average length, $l_X$, along the length of the slit, at an instant, an output, $l_X$, of the element 41 may be expressed by the following equation (1)

$$l_X = l_{oX}(1 - l_X/L_o) \quad \text{......} \quad (1)$$

wherein $l_{oX}$ is the output of the element 41 when the pellet shadow is not present on the slit 14'. Likewise on XZ plane, $$l_Y = l_{oY}(1 - l_Y/L_o) \quad \text{......} \quad (2)$$

When the width, d, is so small that the sub-volumes of a pellet which are of equal width, d, each may be approximated by a volume defined by $k \cdot l_X l_Y d$, wherein k is constant, and when the difference between the speed of a pellet at a time, $t_1$, where a shadow of the pellet enters the slit and the speed at a time, $t_2$, where a shadow of the pellet passes away from the slit, is negligible with respect to an average speed, $\bar{v}$, of the pellet in passing through the volume, V, of a pellet may be expressed by the following equation (3)

$$V = k\bar{v} \int_{t_1}^{t_2} l_X \cdot l_Y dt \quad \text{......} \quad (3)$$

It follows that the volume measurement can be completed in a very short time interval during which the dropping pellet passes away from the beam, and the main factor which reduces the measurement accuracy is the aforesaid speed difference. Therefore, using such a device in the method of the invention, though having simple construction, it is possible to measure the apparent specific gravities of pellets in sequence at a very high rate.

It will be appreciated from the foregoing description that one feature of the present invention provides a system for controlling an iron ore pelletizing and pellet processing operation in dynamic response to an evaluation of the apparent specific gravity (or apparent density) distributions of dry and fired pellets sampled from one process stream, wherein certain pretreating and pelletizing parameters are readjusted so as to impart into the dry pellets an apparent specific gravity distribution optimized for the composition and size distribution of the starting material, and certain firing parameters also are readjusted by taking into account the apparent specific gravity distribution of the resulting dry pellets so as to impart into the fired pellets a desired apparent specific gravity distribution which provides a reliable basis for estimating the quality of the final product as the blast furnace charge composition, and another feature of the invention provides an instrument capable of measuring the apparent specific gravities of pellets in sequence at a high rate and effective to efficiently increase the performance of such a system employing the same.

The method according to the present invention will be described referring to FIG. 10 in which the method is applied to a plant A having steps employing means for a material pretreating step, a disc-type pelletizer, a drying, and a firing furnace.

Figure 10:
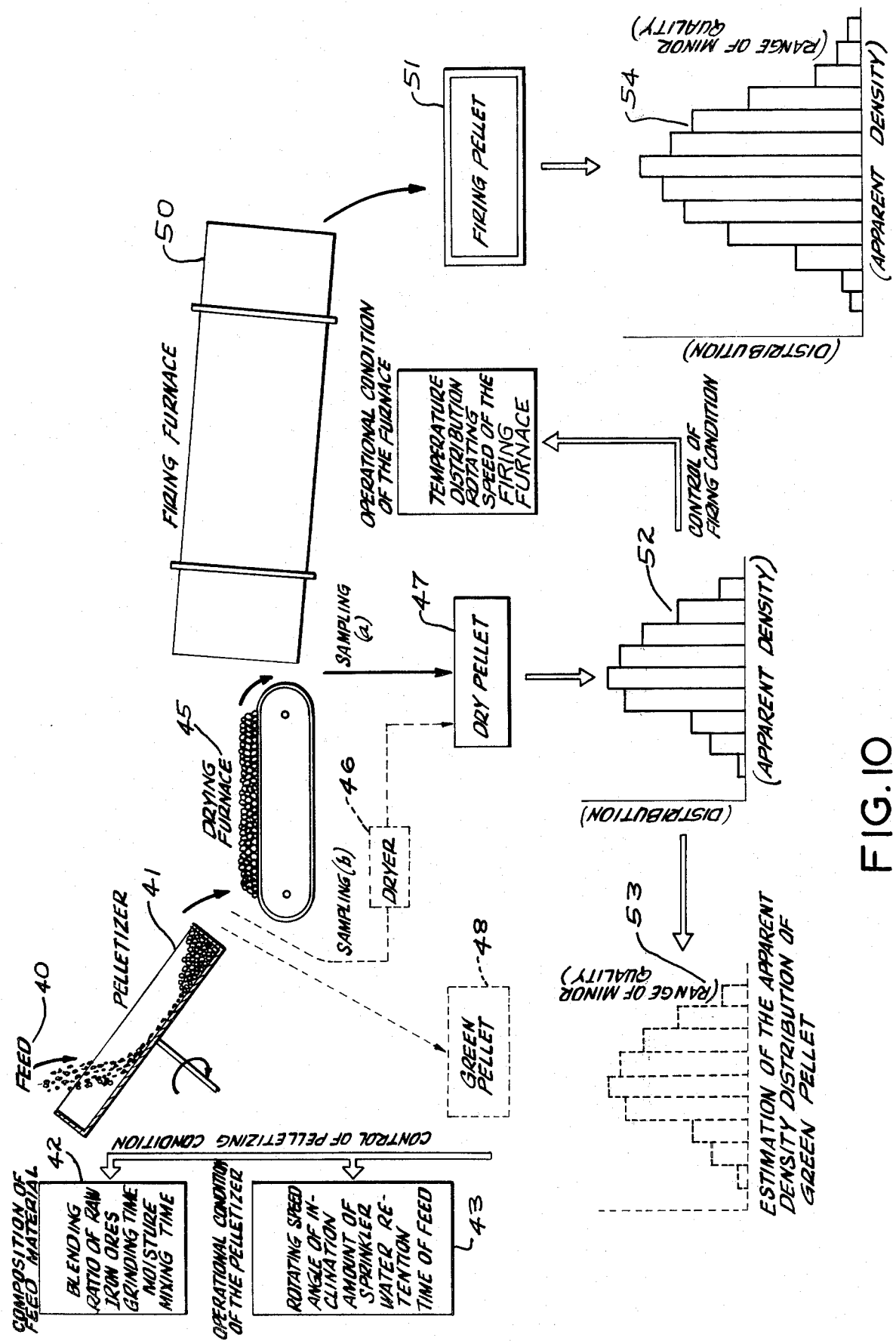
FIG. 10 shows a schematic flow sheet of a plant in which the system of the present invention is adopted.

Referring to FIG. 10, the feed material 40 is supplied to a rotating pelletizer 41. As indicated by blocks 42 and 43, the method controls the pelletizing condition which means that the composition of the feed material and the operational condition of the pelletizer may be controlled according to the analysis of on-stream samples.

The pelletizer then supplies the green pellets to the drying furnace 45. The on-stream dry-pellet sampling may be performed by either sampling step (a) following the drying furnace step by using a separate dryer (shown in dotted lines) 46. The dry pellet sample 47 is analyzed to determine its apparent density distribution 52. From the dry pellet sample 47, the apparent density distribution of the green pellet 48 may be estimated, 53.

When the material to be treated is hematite, the sample (a) for measurement of apparent specific gravity is taken from the pellets discharged from the drying furnace and the apparent specific gravity of 400 to 500 pellets is measured using the apparatus mentioned hereinbefore. The samples may be prepared by drying wet pellets as shown by the sample (b) in FIG. 10.

The volume contraction of the wet pellet during the drying step is very small, or constant with slight variation. Therefore, it is easy to estimate the apparent specific gravity of the wet pellet from that of the dry pellet.

Meanwhile, when the material is magnetite, pre-oxidation is done following the drying in the same apparatus, and thus the sample is taken from the dry pellets before they enter the pre-oxidation zone.

From the distribution analysis, comparison is made to a predetermined standard. When deviations are excessive, the firing condition of the firing furnace 50 is controlled in an attempt to maintain the same fired pellet distribution 54.

Thus, when the estimated apparent specific density distribution of the wet pellet shifts from the distribution to be maintained constant, the operator makes operational measures in his judgment as to which factor of the material composition and the pelletizing conditions should be changed. These factors include the mixing proportions of individual materials, the grinding time, the mixing time, the water content, etc., and the rotation speed of the pelletizer, the inclination angle of the pelletizer, the amount of water supply, the traveling time of the material in the pelletizer.

Meanwhile, in order that the dry pellets from the dryer, which are being charged in the firing furnace, are fired into fired pellets having a predetermined apparent specific gravity distribution, the operational conditions of the firing furnace must be adjusted so as to agree with the apparent specific gravity distribution of the dry pellets to be charged. For this adjustment, the rotation speed and the oil combustion rate and the air supply, etc., which control the temperature distribution in the furnace are changed, and these changed conditions are maintained until the apparent specific gravity distribution of the dry pellets returns to its original distribution by adjustment of the material preparation and the pelletizing conditions.

In this way, the apparent specific gravity distribution of the fired pellets is maintained constant and thus pellets having desirable metallurgical properties can be produced consistently.

The following example further serves to illustrate the present invention as applied in the aforesaid pellet manufacturing plant A.

Example:

A mixture of iron ores of different source as the starting material which was received a certain time ago and had been used ever since had a chemical composition and a size distribution shown in Column B of Table 1. In the earlier stage of a production run, the starting material was mixed with 9.3% by weight of water, and was fed at a relatively high rate of 8.5 tons/hr. to a pelletizer which was operated to permit a relatively short retention time of 5.5 minutes. The employed rotary kiln were operated under normal conditions at a maximum temperature of 1,280° C. and a rate of rotation of 40 rpm. The final product had a high cold crushing strength, high susceptibility to reduction and low expansion rate as shown in Column I of Table 2. The apparent specific gravity distributions of the dry and fired pellets sampled in this earlier state are shown in FIGS. 11a and 11a', respectively.

Figure 11:
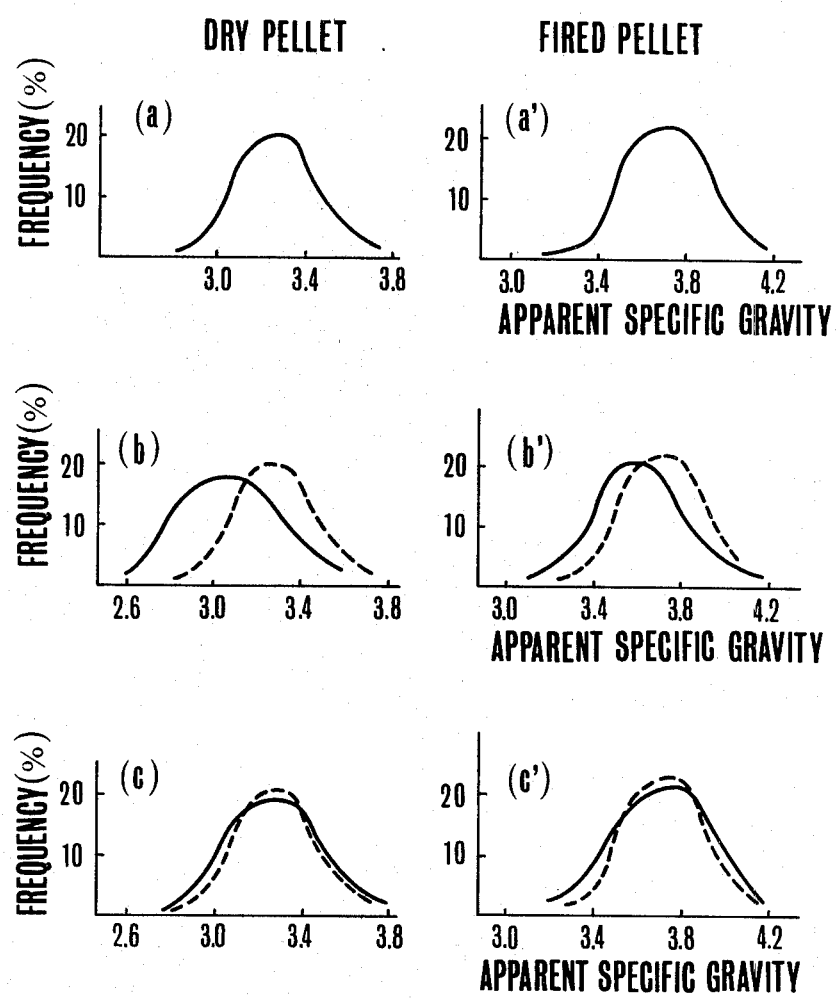
FIG. 11 is a graph illustrating the effectiveness of the present invention in controlling process factors.

So more than a half of the production run had passed, and at this time the apparent specific gravity distribution of the dry pellets was suddenly shifted to the lower side as shown by a solid line curve in FIG. 11b, wherein the initial distribution is indicated by dashed lines, being equal to the solid line curve in FIG. 11a. We have been informed that when such dry pellets having decreased apparent specific gravities are burned under the normal conditions, lowered crushing strengths and increased expansion rates are imparted into the fired pellets. In order to avoid this, it was necessary to increase the burning temperature. For this reason, the maximum temperature of the rotary kiln was increased to 1,320° C. and simultaneously the rate of rotation was increased to 48 rpm to prevent the ring formation in the kiln, these and other new firing parameter being shown in Column II of Table 2. By such alternations of the firing parameters, a distribution of the new fired pellets indicated by a solid line curve in FIG. 11b' was effected which is located considerably near the initial distribution indicated by dashed lines identical to the curve in FIG. 11a', and the decrease in crushing strength could be restricted to about 30kg.

Table 2

|  | I | II | III |
|---|---|---|---|
| Pretreating parameter: |  |  |  |
| Water content (%) | 9.3 | 9.3 | 8.8 |
| Mixing time (min.) | 4.5 | 4.5 | 4.5 |
| Pelletizing parameter: |  |  |  |
| Feeding rate (t/hr.) | 85 | 85 | 60 |
| Rotation rate (rpm) | 9.5 | 9.5 | 10.0 |
| Retention time (min.) | 5.5 | 5.5 | 6.5 |
| Firing parameter: |  |  |  |
| Maximum temperature (° C) | 1,280 | 1,320 | 1,280 |
| Rotaton rate (rpm) | 40 | 48 | 40 |
| Retention time (min.) | 40 | 35 | 40 |
| Fired pellet property: |  |  |  |
| Cold crushing strength (kg) | 314 | 286 | 310 |
| Reduction rate (%) | 87.2 | 88.5 | 87.5 |
| Expansion rate (%) | 12.3 | 13.8 | 12.7 |

Firing parameters given in Column II of Table 2 are disadvantageous for the rotary kiln which are to be operated for a long period, because of the shortening of their life-times and an increase of the combustion fuel supply rate. From the economical point of view, it is preferred to alter certain pretreating and pelletizing parameters instead of such alternation of the firing parameters. On this account, we decided that the pretreating and pelletizing parameters should be altered subsequent to the alternation of the firing parameters, the new parameters being shown in Column II of Table 2. Then, considering that the decreases in the apparent specific gravities of the dry pellets were due to decreases in the grain sizes of the mixed iron ores, we initiated the change by decreasing the addition of water to the starting material and the feeding rate of the mixture to the pelletizer and increasing the retention time of the mixture in the pelletizer so as to produce high density green pellets. In this case, the efficiency of the pelletizer was decreased, which, however, was compensated by an increase in the number of employed pelletizers. In a time interval of as short as 30 minutes after the initiation of alternation of the pretreating and pelletizing parameters, the apparent specific gravity distribution of the dry pellets produced from the new green pellets became almost identical to the initial one as shown in FIG. 11c wherein the initial distribution is indicated by dashed lines. As the apparent specific gravity distribution of the dry pellets approached to the initial one, the firing parameters were altered to the initial ones shown in Column I of Table 2.

The present invention and method have been described in connection with examples using disc-type pelletizers and grate-kiln type firing furnaces. It should be understood that the invention can be effectively applied to systems using other types of pelletizers and firing furnaces.

Figure 9:
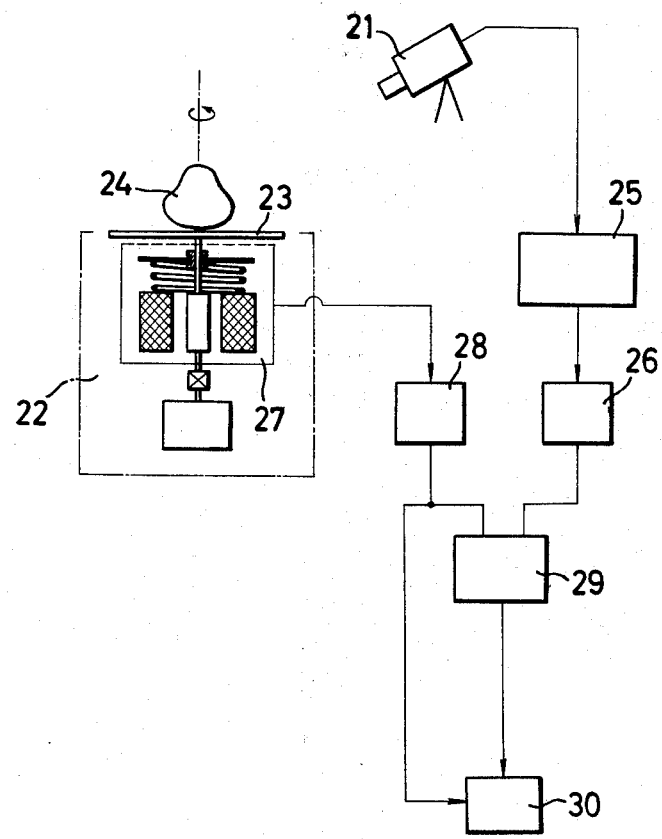
FIG. 9 shows a modification of the instrument shown in FIGS. 6, 7 and 8 in which a television image pickup tube is used in place of the photoelectric element.

Further, it is possible to measure the apparent specific gravity of the pellet using a television image pick-up tube shown in FIG. 9 instead of the photoelectric element shown in FIGS. 6, 7 and 8. In FIG. 9, 21 is a television camera which photographs sample pellets 24 on the table 23 of the sample stand 22 to obtain outputs in proportion to the projected cross-section. The outputs are sent to the volume measurement device 25 as video signals. 26 is a sample holding circuit which holds the volume proportion signals. 27 is a weight measurement device composed of differential transformers arranged on the sample stand 22; 28 is a differential amplifying device, and these devices produce weight proportion signals. 29 is a computing device which computes the apparent specific gravity of the sample 24 on the basis of the proportion of the volume and weight proportion signals. 30 is a recorder.

The volume V of the sample pellet is given by the following formula from the mean projected cross-section S on the assumption that the sample is a spherical body.

$$V = \frac{4}{3} \frac{1}{\sqrt{\pi}} S^{\frac{3}{2}} = KS^{\frac{3}{2}}$$

What is claimed is:

1. In a method of controlling an iron ore pelletizing and pellet processing operation in accordance with an evaluation of the dry and fired pellets sampled from a process stream, having material pretreating, pelletizing, drying and firing steps, said steps having predetermined control parameters associated therewith, the improvement comprising the steps of:
   a) periodically cutting a dry pellet sample from the process stream in sequence;
   b) measuring the apparent specific gravity of each of the dry pellet samples to find a distribution thereof;
   c) comparing the apparent specific gravity distribution of said measured sample with a predetermined apparent specific gravity distribution standard;
   d) readjusting the material pretreating, and pelletizing control parameters when the measured apparent specific gravity departs excessively from the predetermined standard, said readjustment for returning the apparent specific gravity of the dried pellets to the predetermined standard;

e) temporarily readjusting said predetermined firing control parameters of the firing furnace so as to compensate for the measured apparent specific gravity of the dry pellet samples to produce a fired pellet having desired apparent specific gravity distribution, said firing control parameters being readjusted until the dried pellet samples return to the predetermined standard; and f) returning said firing control parameters to the predetermined values.

2. The method of claim 1 wherein said predetermined material pretreating control parameters to be readjusted include at least one of the mixing proportions of individual materials, the grinding time, the mixing time, the water content and the predetermined pelletizing control parameters include the rotation speed of the pelletizer, the inclination angle of the pelletizer, the amount of water supply and the travelling time of the material in the pelletizer.

3. The method of claim 1 wherein the predetermined firing parameters to be readjusted include at least one of the rotation speed, the fuel combustion rate and the air supply of the furnace.

4. The method of claim 1 wherein a preoxidation step is included and the dried pellet samples are obtained after the drying step but prior to the preoxidation step when magnetite ore is used.

5. The method of claim 1 wherein the dried pellet samples are obtained by first taking wet pellets prior to drying and drying them in a separate step when hematite ore is used.

* * * * *